(12) United States Patent  
Glazer et al.

(10) Patent No.: US 9,402,566 B2  
(45) Date of Patent: Aug. 2, 2016

(54) ORTHOPEDIC MEASUREMENT DEVICES, SYSTEMS AND METHODS

(71) Applicant: Tenzin LLC, Chestnut Hill, MA (US)

(72) Inventors: Paul Andrew Glazer, Chestnut Hill, MA (US); David Ray, Norfolk, MA (US); Joseph Ting, Acton, MA (US)

(73) Assignee: Tenzin LLC, Chestnut Hill, MA (US)

( * ) Notice: Subject to any disclaimer, the term of this patent is extended or adjusted under 35 U.S.C. 154(b) by 300 days.

(21) Appl. No.: 13/905,789

(22) Filed: May 30, 2013

(65) Prior Publication Data

US 2014/0066810 A1    Mar. 6, 2014

Related U.S. Application Data

(60) Provisional application No. 61/695,578, filed on Aug. 31, 2012.

(51) Int. Cl.
*A61B 5/107* (2006.01)
*A61B 17/70* (2006.01)

(52) U.S. Cl.
CPC ........... *A61B 5/1076* (2013.01); *A61B 17/7074* (2013.01)

(58) Field of Classification Search
CPC .......................... A61B 19/46; A61B 2019/461
See application file for complete search history.

(56) References Cited

U.S. PATENT DOCUMENTS

| | | | |
|---|---|---|---|
| 4,987,904 A | 1/1991 | Wilson | |
| 5,013,318 A * | 5/1991 | Spranza, III | 606/102 |
| 5,158,096 A | 10/1992 | Clark et al. | |
| 5,291,900 A | 3/1994 | Lowenstein | |
| 6,105,269 A | 8/2000 | Kondrat | |
| 6,193,724 B1 | 2/2001 | Chan | |
| 6,500,179 B1 | 12/2002 | Masini | |
| 6,637,278 B1 | 10/2003 | Fasanella | |
| 6,979,299 B2 | 12/2005 | Peabody et al. | |
| 7,134,216 B2 | 11/2006 | Rupp et al. | |
| 7,172,599 B2 | 2/2007 | Steffensmeier et al. | |
| 2002/0129509 A1* | 9/2002 | Evans, III | 33/757 |
| 2002/0198471 A1 | 12/2002 | Baxter-Jones et al. | |
| 2003/0181920 A1* | 9/2003 | Hawkins et al. | 606/102 |
| 2008/0167542 A1 | 7/2008 | Lampropoulos et al. | |
| 2011/0071437 A1 | 3/2011 | Merchant | |

OTHER PUBLICATIONS

Search Report and Written Opinion issued in PCT/US2013/056844 on Nov. 20, 2013.

* cited by examiner

*Primary Examiner* — Adam J Eiseman
*Assistant Examiner* — Patrick Fernandes
(74) *Attorney, Agent, or Firm* — Locke Lord LLP; Joshua L. Jones; Alicia J. Carroll

(57) ABSTRACT

A device for orthopedic measurements includes a main housing, a center member, a measurement indicator, and a flexible member. The main housing has a proximal end with a top opening and a distal end with a side opening, and defines a longitudinal axis and includes a main housing cavity. The center member is disposed along the longitudinal axis within the main housing cavity. The measurement indicator is operatively connected to the center member, and is configured and adapted to display a measurement of a distance. The flexible member is threaded through the main housing cavity, and includes a first end and an opposed second end with an eyelet disposed proximate the side opening of the main housing. The eyelet is configured to be drawn away from the main housing, extending the flexible member outward with respect to the side opening to display a measurement on the measurement indicator.

8 Claims, 11 Drawing Sheets

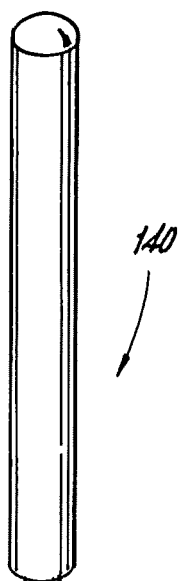
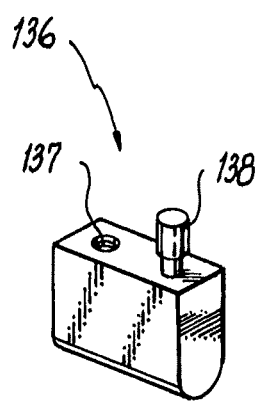
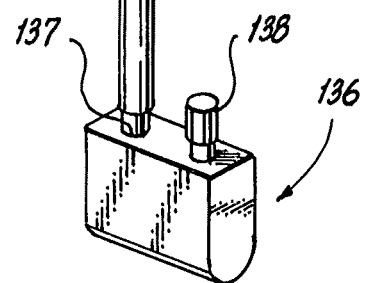
Fig. 5
Fig. 4

Fig. 12
Fig. 13
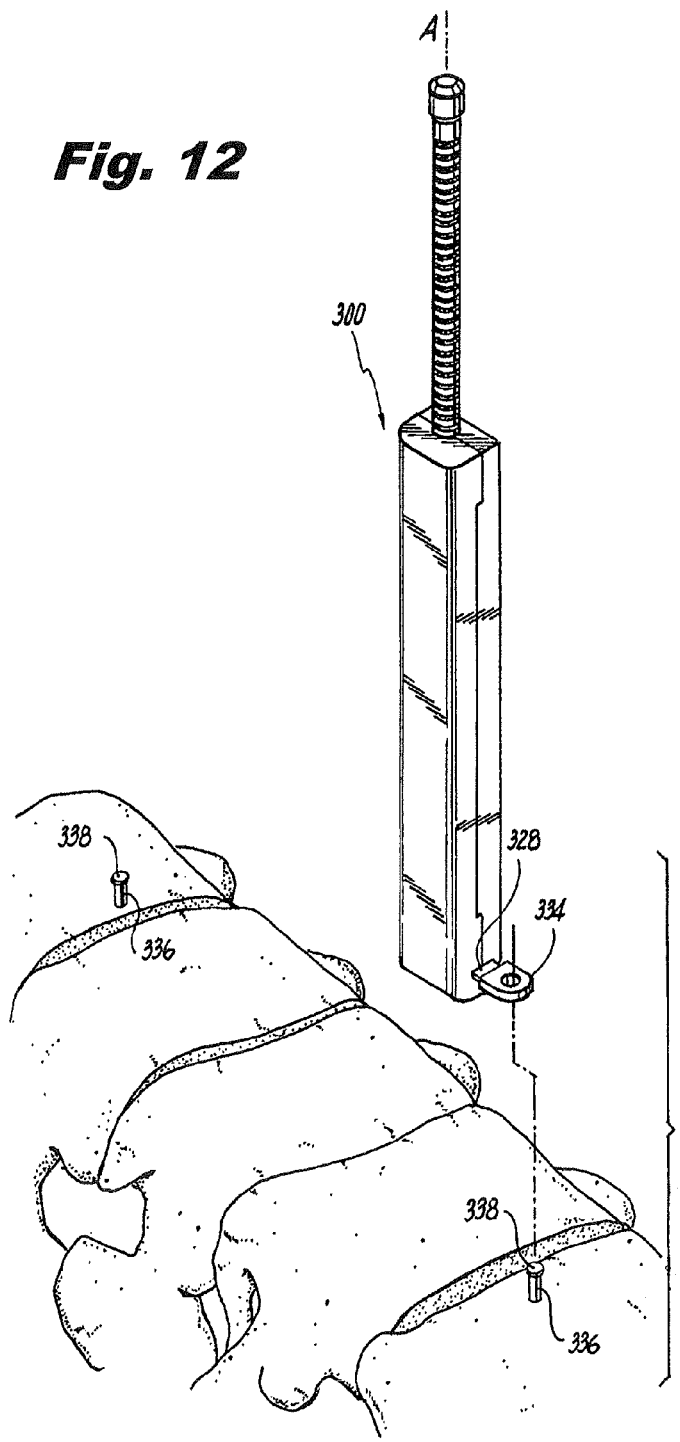
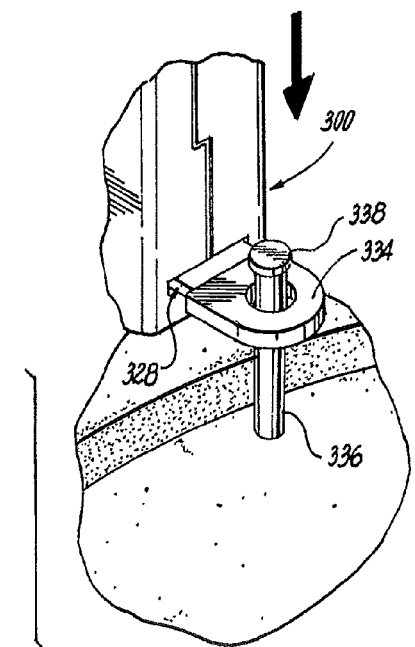

ORTHOPEDIC MEASUREMENT DEVICES, SYSTEMS AND METHODS

CROSS-REFERENCE TO RELATED APPLICATIONS

This application claims priority to U.S. Provisional Patent Application No. 61/695,578 filed Aug. 31, 2012 which is incorporated by reference herein in its entirety.

BACKGROUND OF THE INVENTION

1. Field of the Invention

The present invention relates to orthopedic surgical procedures and more particularly to methods and apparatuses for orthopedic measurements.

2. Description of Related Art

Presently, there is no known way to accurately measure the proper size for an orthopedic prosthesis implant, such as a cervical plate, or the like. Traditional methods to determine the correct size require trial and error. As one example, anterior cervical decompression and fusion is performed through a small transverse skin incision in the front of the neck. The procedure involves the removal of one or more spinal discs to decompress the spinal cord and exiting nerve roots. The spinal disc heights are increased because the discs are replaced with bone grafts to decompress the exiting nerve roots. Before placing the grafts, the surgeon templates for the height of the disc spaces with wedges, or spacers, of known dimensions. The spacers are then removed and the grafts are placed. Following the placement of grafts, the surgeon must tunnel a long cervical plate down to the spine for fusions of one or more disc spaces. The length of the plates is minimized in order to avoid adjacent segment degeneration, making accuracy crucial. Often, the first plate chosen and placed in position is either too short or too long. In order to determine the correct plate, a surgeon must remove the incorrect length plate and try another size plate. This method of trial and error requires additional soft tissue retraction causing additional trauma to the tissue resulting in longer recovery time and increased scar tissue. It also increases the time required to perform the procedure and the chance of concomitant risks.

Such conventional methods and systems have generally been considered satisfactory for their intended purpose. However, there is still a need in the art for methods and apparatuses that allow for improved accuracy in orthopedic measurement, e.g., when performing anterior cervical decompression and fusion, when determining the proper size for an orthopedic prosthesis implant or the like. There also remains a need in the art for such methods and apparatuses that are easy to make and use. The present invention provides a solution for these problems.

SUMMARY OF THE INVENTION

The subject invention is directed to a new and useful device for orthopedic measurements. The device includes a main housing, a center member, a measurement indicator, and a flexible member.

The main housing has a proximal end and a distal end, the proximal end having a top opening and the distal end having a side opening, wherein the main housing defines a longitudinal axis and includes a main housing cavity. The center member is disposed along the longitudinal axis within the main housing cavity, wherein the center member is configured and adapted to move along the longitudinal axis relative to the main housing. The measurement indicator is operatively connected to the center member, and is configured and adapted to display a measurement of a distance. The flexible member includes a first end and an opposed second end. The second end has an eyelet. The flexible member is threaded through the main housing cavity and the eyelet is disposed proximate the side opening of the main housing. The eyelet is configured and adapted to be drawn away from the main housing, extending the flexible member outward with respect to the side opening to display a measurement on the measurement indicator.

In accordance with certain embodiments, the device for orthopedic measurements can include a spring disposed in the main housing cavity along the longitudinal axis between the side opening and the top opening. The spring can be operatively connected to bias the center member along the longitudinal axis away from the distal end of the main housing. Further, the spring can be disposed between the top opening and the flexible member, and can surround and operatively connect to the center member. Or, the spring can be disposed between a distal end of the center member and the distal end of the main housing, operatively connected to the center member. In both cases, the spring can be biased along the longitudinal axis such that the flexible member is biased toward an undeployed position.

In further accordance with certain embodiments, the flexible member can be operatively connected to the center member, and/or can be operatively connected to the distal end of the center member and threaded through the spring along the longitudinal axis, so that movement of the center member against a bias force of the spring along the longitudinal axis drives the flexible member outward through the side opening.

In further accordance with certain embodiments, a portion of the center member can extend out of the main housing through the top opening at the proximal end. The measurement indicator can be at least partially disposed on the portion of the center member that extends out of the main housing. In addition, the main housing cavity can include a cammed surface between the center member and the distal end of the main housing, wherein the cammed surface can be configured and adapted to guide the flexible member in and out of the main housing through the side opening-substantially orthogonal to the longitudinal axis of the main housing. Further, the eyelet can be disposed outside of the main housing cavity and can be larger than the side opening to prevent it from being drawn into the main housing cavity.

The subject invention is also directed to a new and useful method of performing orthopedic measurements. The method includes inserting a measurement tool into an incision, securing an eyelet of the measurement tool on a tack, the eyelet being operatively connected to a flexible member, moving the measurement tool away from the tack, wherein the movement deploys the flexible member, and displaying a measurement indicative of the distance between the measurement tool and the tack.

The subject invention is also directed to a device for orthopedic measurements that can measure between, for example, two tacks, spacers, or the like. The device includes a main housing that has a proximal end and a distal end, the proximal end has a top opening and the distal end has opposed first and second side openings. The main housing defines a longitudinal axis and includes a main housing cavity. The device also includes a center member disposed along the longitudinal axis within the main housing cavity. A portion of the center member extends out of the main housing through the top opening at the proximal end. The center member is configured and adapted to move along the longitudinal axis relative to the main housing. The device also includes a measurement indicator operatively connected to the center member and configured and adapted to display a measurement of a distance. The device also includes a cable including a first and a second end. Each cable end has an eyelet. The cable is threaded through the main housing cavity and the eyelets are disposed proximate the first and second side openings, respectively, of the main housing. The eyelets are configured and adapted to be drawn away from the main housing, extending the cable outward with respect to the side openings, and displaying a measurement on the measurement indicator.

In accordance with certain embodiments, the measurement indicator can be much as described above. The device can also include a center pulley wheel disposed on the center member within the main housing cavity between the measurement indicator and the distal end along the longitudinal axis. The center pulley wheel can be configured and adapted to move with the center member along the longitudinal axis relative to the main housing and to rotate about a pulley axis. The device can further include a spring disposed in the main housing cavity along the longitudinal axis between the center pulley wheel and the distal end. The spring can be configured and adapted to bias the center member along the longitudinal axis away from the distal end of the main housing. The device can also include two side pulleys. A first side pulley wheel can be mounted within the main housing cavity proximate the first side opening configured and adapted to rotate about a pulley axis. A second side pulley wheel can be mounted within the main housing cavity proximate the second opening configured and adapted to rotate about a pulley axis. The cable can be threaded through the first and second side pulley wheels, such that the first end extends through the first side opening and the second end extends through the second side opening, thereby moving the center pulley wheel and the center member along the longitudinal axis relative to the main housing against the bias force of the spring when either or both of the eyelets extend outward, and display a measurement on the measurement indicator.

In further accordance with certain embodiments, the cable can be threaded between the center pulley wheel and the center member. The first end can be threaded down through the main housing cavity, around the first side pulley wheel, and out through the first side opening. The second end can be threaded down through the main housing cavity, around the second side pulley wheel and out through the second side opening. The eyelets can be disposed outside of the main housing cavity flush with the main housing and can be larger than the first and second side openings to prevent them from being drawn into the main housing cavity.

The invention also provides a method of performing orthopedic measurements, for example, between two tacks, spacers, or the like. The method includes inserting a measurement tool into an incision, securing a first eyelet of the measurement tool on a first spacer post, e.g. embedded in a spine or other orthopedic location, moving the measurement tool away from the first spacer post towards a second spacer post, securing a second eyelet of the measurement tool to the second spacer post, and displaying a measurement indicative of the distance between the spacer posts, for example, to aid in determining the proper size for an orthopedic prosthesis implant or the like.

The invention also provides a kit for performing orthopedic measurements. The kit includes a device for orthopedic measurements, as described above, a plurality of spacers with posts, and a removable spacer placement tool configured and adapted to enter an incision and place the spacers.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 4 is a perspective view of an exemplary embodiment of a spacer constructed in accordance with the present invention;

FIG. 5 is a perspective view of an exemplary embodiment of a removable spacer placement tool constructed in accordance with the present invention, showing the tool threaded into the spacer of FIG. 4;

FIG. 12 is a perspective view of a spinal model showing a first tack and a second tack placed in the spine and the device of FIG. 10;

FIG. 13 is a partial enlarged perspective view of the spinal model of FIG. 12, showing a step of securing an eyelet of the device of FIG. 10 on the first tack;

DETAILED DESCRIPTION OF THE PREFERRED EMBODIMENTS

Figure 1:
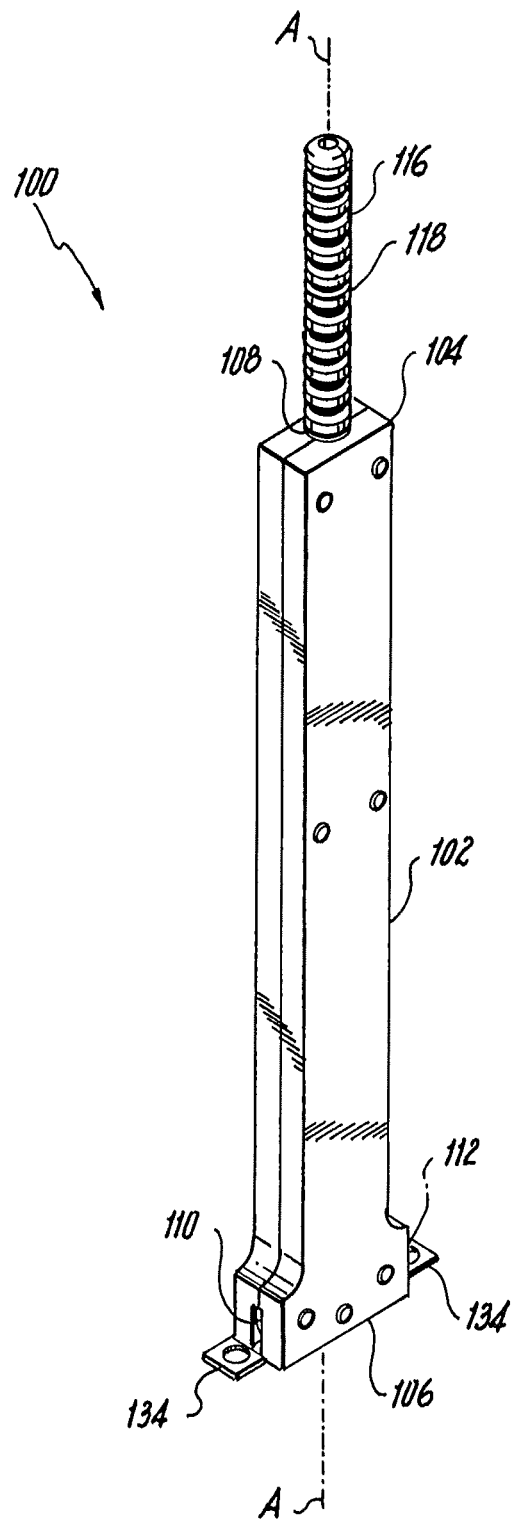
FIG. 1 is a perspective view of an exemplary embodiment of a device for orthopedic measurements constructed in accordance with the present invention.

Reference will now be made to the drawings wherein like reference numerals identify similar structural features or aspects of the subject invention. For purposes of explanation and illustration, and not limitation, a partial view of an exemplary embodiment of the device for orthopedic measurements in accordance with the invention is shown in FIG. 1 and is designated generally by reference character 100. Other embodiments of the device in accordance with the invention, or aspects thereof, are provided in FIGS. 2-15 as will be described.

Referring now to FIG. 1, the subject invention is directed to a new and useful device for orthopedic measurements 100. Device 100 includes a main housing 102 that has a proximal end 104 and a distal end 106, proximal end 104 has a top opening 108 and distal end 106 has opposed first and second side openings 110, 112, respectively. Main housing 102 defines a longitudinal axis A and includes a main housing cavity 114, shown in FIG. 2. Device 100 also includes a center member 116 disposed along longitudinal axis A within main housing cavity 114. A portion of center member 116 extends out of main housing 102 through top opening 108 at proximal end 104. Center member 116 is configured and adapted to move along longitudinal axis A relative to main housing 102. Device 100 also includes a measurement indicator 118 on center member 116. Measurement indicator 118 is at least partially disposed on the portion of the center member 116 that extends out of the main housing 102 and is configured and adapted to display a measurement of a distance with a series of graduations marked around center member 116. Those skilled in the art will readily appreciate that a measurement indicator can instead be digital, dial based or any other suitable type of indicator can be used instead of graduations on a protruding member, without departing from the spirit and scope of the invention.

Figure 2:
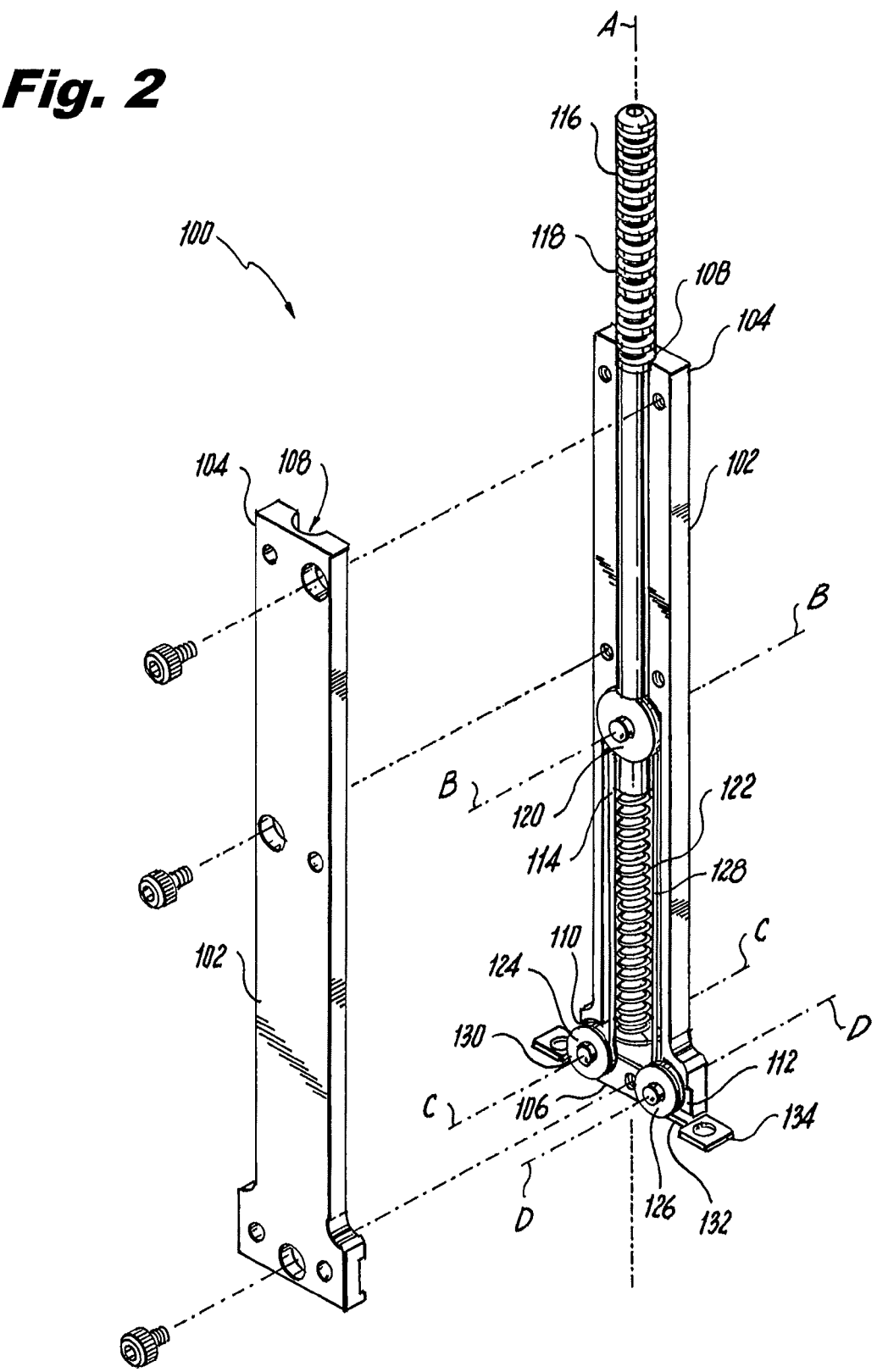
FIG. 2 is an exploded perspective view of the device of FIG. 1.

With reference now to FIG. 2, the device also includes a center pulley wheel 120 disposed on center member 116 within main housing cavity 114 between measurement indicator 118 and distal end 106 along longitudinal axis A. Center pulley wheel 120 is configured and adapted to move with center member 116 along longitudinal axis A relative to main housing 102 and to rotate about a pulley axis B. Device 100 further includes a spring 122 disposed in main housing cavity 114 along longitudinal axis A between center pulley 120 wheel and distal end 106. Spring 122 is configured and adapted to bias center member 116 along longitudinal axis A away from distal end 106 of main housing 102. Device 100 also includes two side pulleys 124, 126. A first side pulley wheel 124 is mounted within main housing cavity 114 proximate first side opening 110 configured and adapted to rotate about a pulley axis C. A second side pulley wheel 126 is mounted within main housing cavity 114 proximate second side opening 112 configured and adapted to rotate about a pulley axis D.

Figure 3:
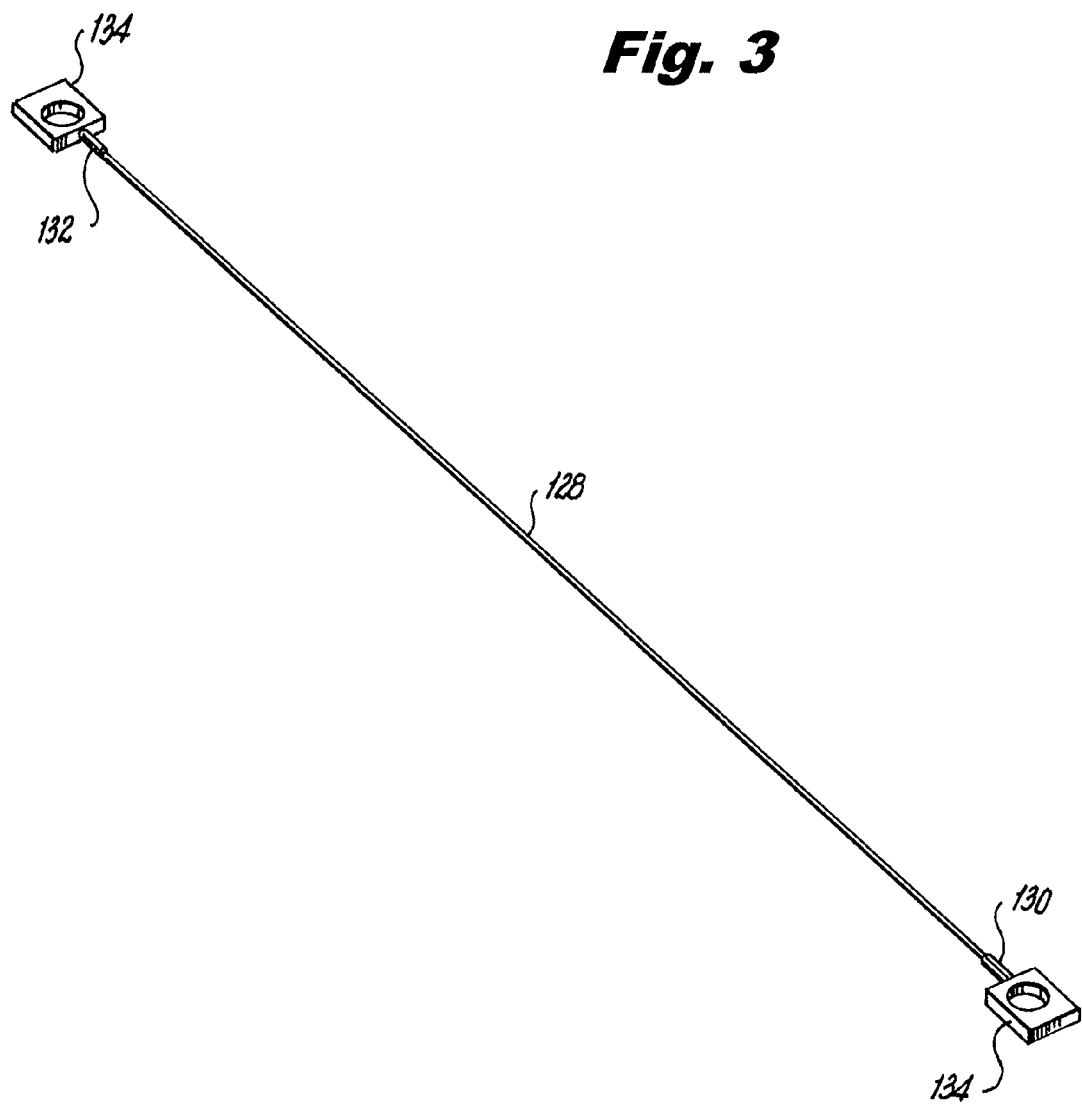
FIG. 3 is a perspective view of a cable of the device of FIG. 1.

Referring now to FIGS. 2 and 3, device 100 also includes a cable 128 including a first end 130 and a second end 132. Each cable end 130,132 has an eyelet 134. FIG. 3 shows cable 128 and eyelets 134 removed from main housing 102. As shown in FIG. 2, cable 128 is threaded through the center pulley wheel 120 and each of first and second side pulley wheels 124,126, such that first end 130 extends through first side opening 110 and second end extends through second side opening 112, and wherein the eyelets 134 are disposed proximate first and second side openings 110,112, respectively, of the main housing 102. Eyelets 134 are configured and adapted to be drawn away from the main housing 102, extending cable 128 outward with respect to side openings 110, 112, thereby moving center pulley wheel 120 and center member 116 inward along longitudinal axis A relative to main housing 102 against the bias force of spring 122 when either or both of the eyelets 134 are extended outward to display a measurement on measurement indicator 118. The measurement can be determined by reading or counting the graduations of measurement indicator 118.

With continued reference to FIG. 2, in accordance with certain embodiments, cable 128 is threaded between center pulley wheel 120 and the center member 116. The first end 130 is threaded down through main housing cavity 114, around first side pulley wheel 124, and out through first side opening 110. Second end 132 is threaded down through main housing cavity 114, around second side pulley wheel 126 and out through second side opening 112. In other words, cable 128 is threaded under the first side pulley wheel 124, over the center pulley wheel 120, and under the second side pulley wheel 126. Eyelets 134 are disposed outside of main housing cavity 114 flush with main housing 102 and are larger than first and second 110, 112 side openings to prevent them from being drawn into main housing cavity 114.

Those skilled in the art will readily appreciate that a device for orthopedic measurements, e.g. device 100, can be disposable, for example, made of a plastic or other disposable material and can be packaged and sold sterile, or it can be reusable and be configured to be cleaned and sterilized.

Referring now to FIGS. 4-8, the invention also provides a method of performing orthopedic measurements. As discussed above, in anterior cervical decompression and fusion, the spinal disc height is increased by placing bone grafts. Traditionally, before placing the grafts, surgeons template for the height of the disc spaces with spacers of known dimensions. As shown in FIG. 4, in accordance with the invention, spacers 136 used to template for the height of the disc spaces have posts 138 to accommodate for using the measurement device, e.g. device 100, therein allowing the spacer to serve two purposes while decreasing the invasiveness of the surgery.

Figure 6:
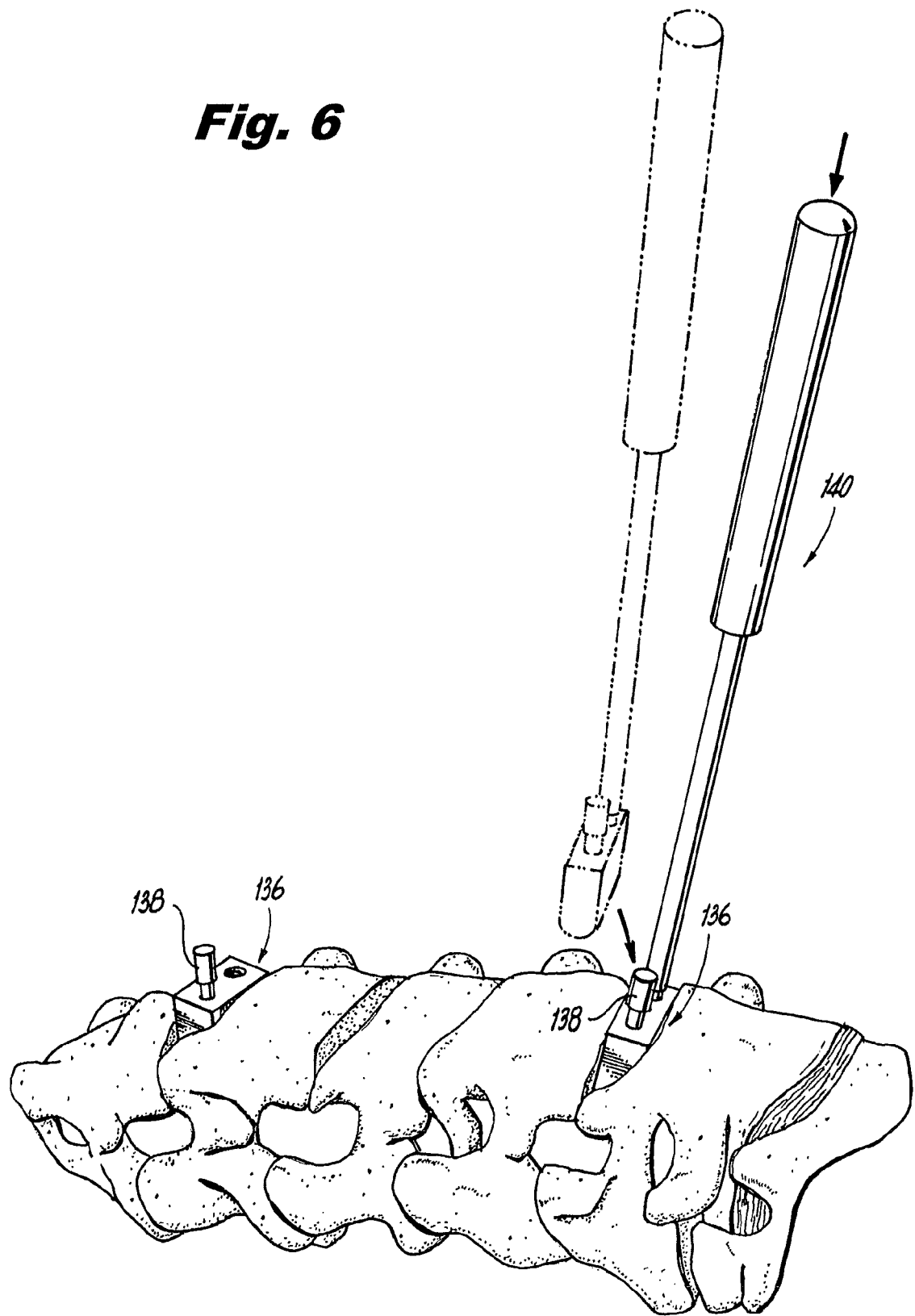
FIG. 6 is a perspective view of a spinal model showing placement of the spacers of FIG. 4 in the spine and showing the removable spacer placement tool of FIG. 5.

Referring to FIGS. 5 and 6, spacer 136 is affixed to a removable spacer placement tool 140, which is threaded into threaded bore 137 of spacer 136 in FIG. 5. The removable spacer placement tool, e.g. placement tool 140, implants the first spacer, e.g. spacer 136, into a spinal disc space, as shown in FIG. 6. It is then unthreaded, and removed from the spacer, leaving the first spacer implanted. The same placement tool, e.g. placement tool 140, is then threaded into the threaded bore, e.g. threaded bore 137, of a second spacer, e.g. spacer 136, and affixed to the second spacer. The steps described above performed with the first spacer are then repeated with the second spacer.

Figure 7:
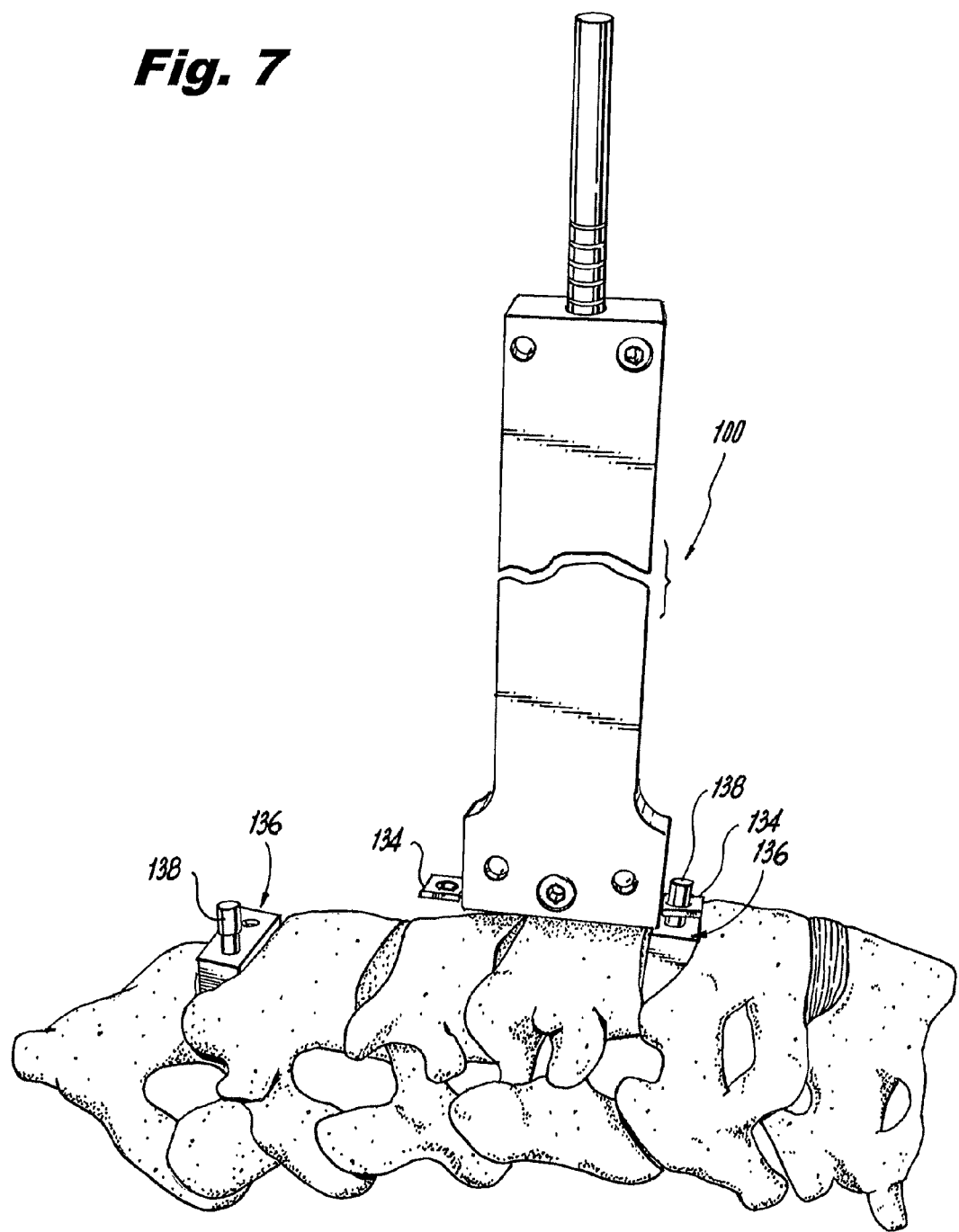
FIG. 7 is a perspective view of the spinal model of FIG. 6, showing a step of hooking a first eyelet on a first spacer.
Figure 8:
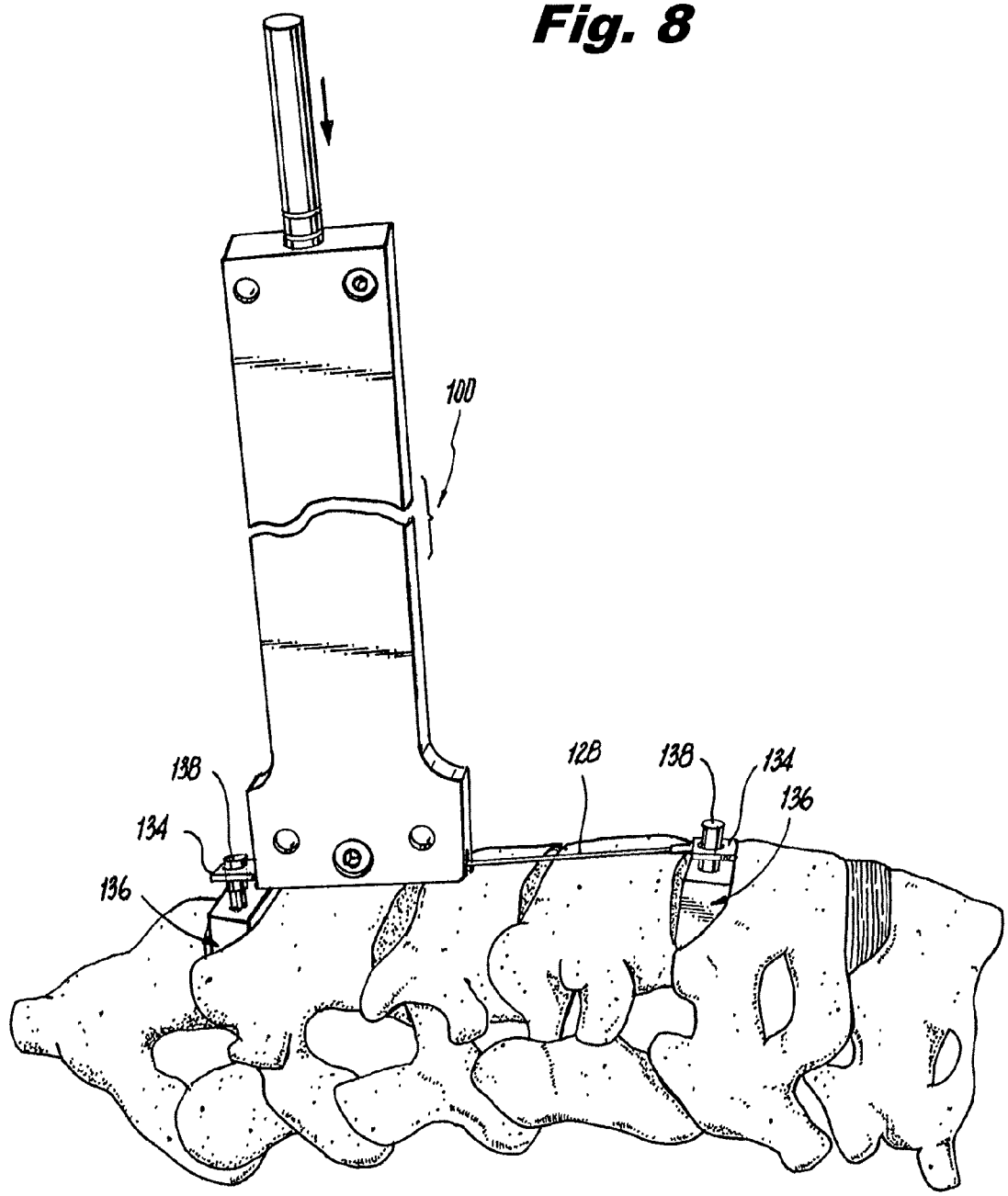
FIG. 8 is a perspective view of the spinal model of FIG. 6, showing a step of hooking a second eyelet on a second spacer to take a measurement.

As shown in FIGS. 7-8, the method includes inserting a measurement tool, e.g. device 100, into an incision, securing a first eyelet, e.g. either of eyelets 134, of the measurement tool on a first spacer post, e.g. post 138, as shown in FIG. 7, moving the measurement tool away from the first spacer post towards a second spacer post, securing a second eyelet, e.g. either of eyelets 134 of the measurement tool to the second spacer post, as shown in FIG. 8, and displaying a measurement indicative of the distance between the spacer posts, for example, to aid in determining the proper size for an orthopedic prosthesis implant or the like.

In addition, those skilled in the art will readily appreciate that the measurement device can be calibrated to display appropriate measurements indicative of the height or length needed for the orthopedic prosthetic implant. For example, if the measurement tool is being used to perform anterior cervical decompression and fusion, the measurement tool, e.g. device 100, can be calibrated to display the distance between the endplates of the one or more spinal discs as opposed to the distance between the spacer posts. Further, those skilled in the art will readily appreciate that instead of substantially vertical posts on the spacers, like those shown in the Figures, the posts can be laterally off-set as compared with the posts shown in FIG. 6. For example, the posts can be shaped to overhang their respective endplates so the posts are located where the bone screws will ultimately be placed. This overhanging post can provide a more accurate measurement between the endplates and can negate the need for calibration.

Those skilled in the art will also readily appreciate that eyelets 134 can also be placed on tacks. For example, tacks can be used to temporarily affix the plates prior to screw fixation. Tacks can be placed in the vertebral body at the superior and inferior ends of the fusion and can directly indicate where the screws to secure the plate will be fixed. By placing the eyelets 134 on tacks, there is no need to add additional length to the measurement because the distance between tacks is a direct indication of the plate length required.

Those skilled in the art will also readily appreciate that the housing, e.g. housing 102, need not be centered between eyelets, e.g. eyelets 134, during a measurement. In other words, the distance measurement reading is constant regardless of relative position of the housing between eyelets.

Figure 9:
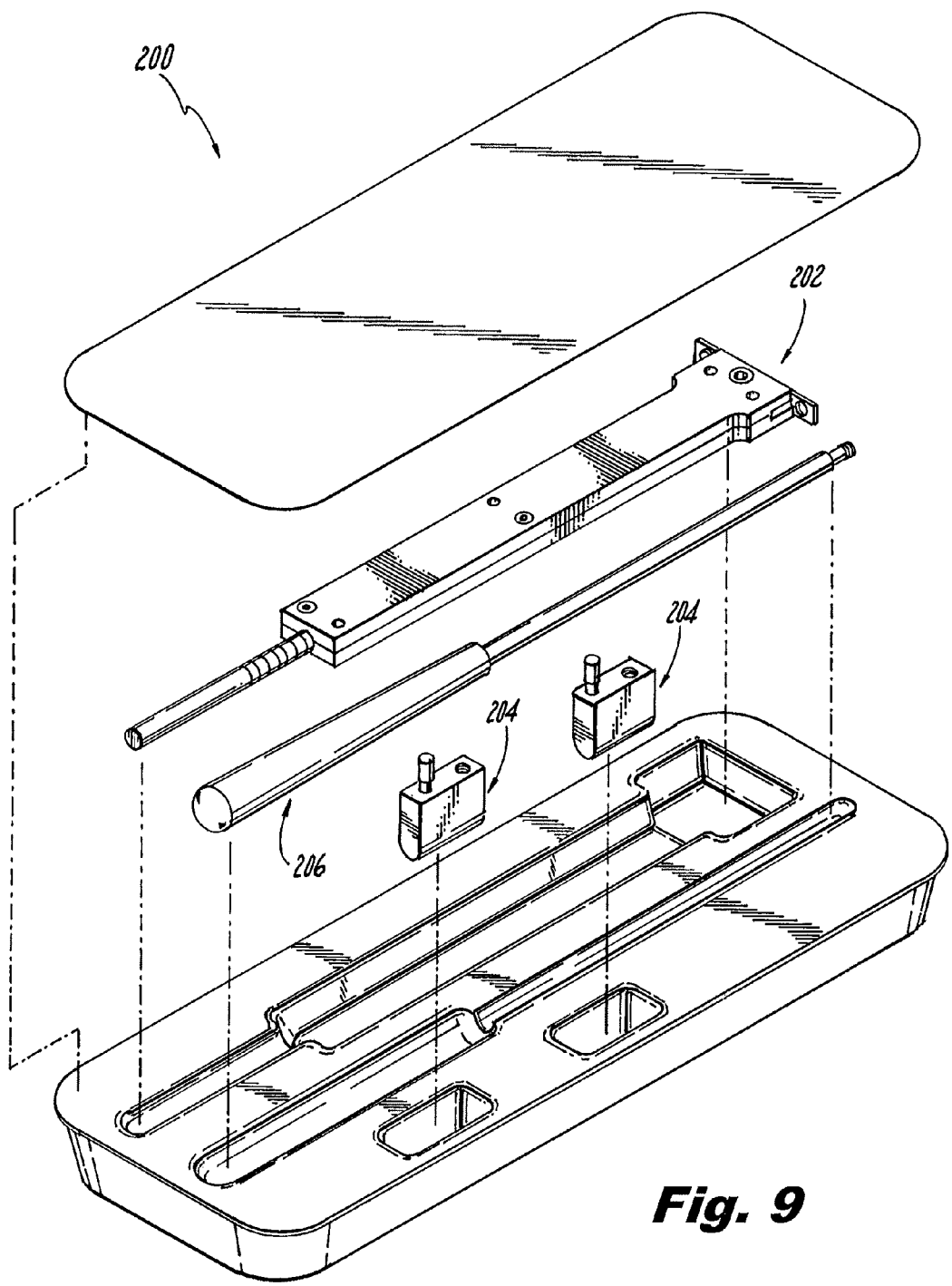
FIG. 9 is an exploded perspective view of an exemplary embodiment of a kit in accordance with the present invention.

Referring to FIG. 9, the invention also provides a kit 200 for performing orthopedic measurements. Kit 200 includes a device for orthopedic measurements 202, a plurality of spacers 204 with posts, and a removable spacer placement tool 206, all as described above.

Figure 10:
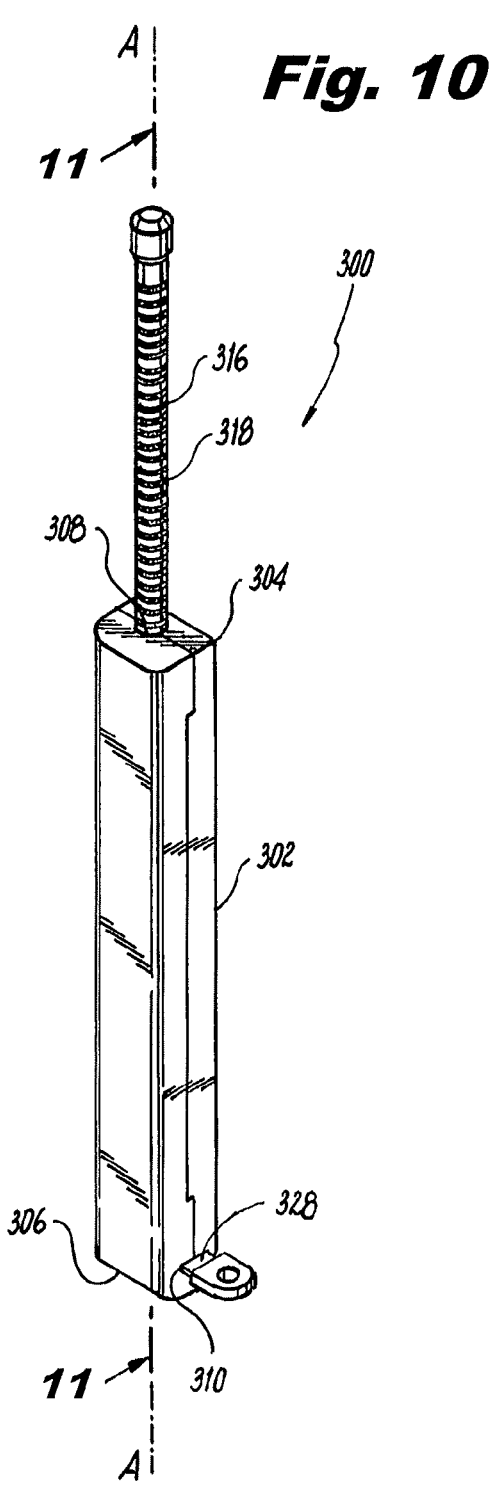
FIG. 10 is a perspective view of another exemplary embodiment of a device for orthopedic measurements constructed in accordance with the present invention.

Referring to FIG. 10, another embodiment of a new and useful device 300 for orthopedic measurements is shown. Device 300 includes a main housing 302, a center member 316, a measurement indicator 318, and a flexible member 328. Main housing 302 has a proximal end 304 and a distal end 306, proximal end 304 having a top opening 308 and distal end 306 having a side opening 310, wherein main housing 302 defines a longitudinal axis A and includes a main housing cavity 314, shown in FIG. 11. Center member 316 is disposed along longitudinal axis A within main housing cavity 314, wherein center member 316 is configured and adapted to move along longitudinal axis A relative to main housing 302. Measurement indicator 318 is operatively connected to center member 316, and is configured and adapted to display a measurement of a distance. Measurement indicator 318 is similar to measurement indicator 118 and its variations, as described above, and can be similarly calibrated. A portion of center member 316 extends out of main housing 302 through top opening 308 at proximal end 304. Measurement indicator 318 is at least partially disposed on the portion of center member 316 that extends out of main housing 302.

Figure 11:
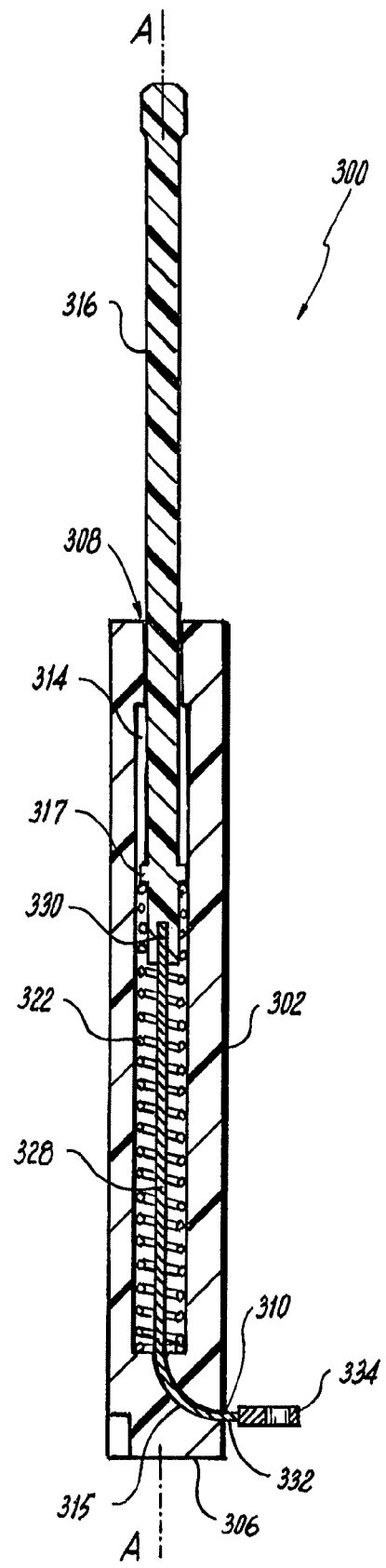
FIG. 11 is a cross-sectional view of the device of FIG. 10, showing a flexible member and spring within a main housing cavity.

Referring now to FIG. 11, flexible member 328 includes a first end 330 and an opposed second end 332. Second end 332 has an eyelet 334. Flexible member 328 is threaded through main housing cavity 314 and eyelet 334 is disposed proximate side opening 310 of main housing 302. Main housing cavity 314 includes a cammed surface 315 between center member 316 and distal end 306 of the housing. Those skilled in the art will readily appreciate that cammed surface 315 is configured and adapted to guide flexible member 328 in and out of main housing 302 through side opening 310 substantially orthogonal to longitudinal axis A of main housing 302. Eyelet 334 is configured and adapted to be drawn away from main housing 302, extending flexible member 328 outward with respect to side opening 310 to display a measurement on measurement indicator 318. Eyelet 334 is disposed outside of main housing cavity 314 and is larger than side opening 310 to prevent it from being drawn into main housing cavity 314.

With further reference to FIG. 11, device 300 for orthopedic measurements includes a spring 322. Spring 322 is operatively connected to bias center member 316 along longitudinal axis A away from distal end 306 of main housing 302. Spring 322 is disposed between a distal end 317 of center member 316 and distal end 306 of the housing, operatively connected to center member 316. Flexible member 328 is operatively connected to distal end 317 of center member 316 and threaded through spring 322 along the longitudinal axis, so that movement of center member 316 against a bias force of spring 322 along longitudinal axis A drives flexible member 328 outward through side opening 310. Those skilled in the art will readily appreciate that the movement of center member 316 against the bias force of spring 322 is not required for deployment of flexible member 328. For example, those skilled in the art will readily appreciate that the force generated by pulling device 300 away from tack 336, while eyelet 334 is affixed to tack 336, as described below, would be sufficient to bias spring 322 and deploy flexible member 328.

Those skilled in the art will readily appreciate that spring 322 can be disposed anywhere in main housing cavity 314 along longitudinal axis A between side opening 310 and top opening 308. For example, those skilled in the art will readily appreciate that spring 322 can be disposed between top opening 308 and flexible member 328, and can surround and operatively connect to center member 316, or can be in any suitable arrangement so that spring 322 is biased along longitudinal axis A such that flexible member 328 is biased toward an undeployed position. Furthermore, those skilled in the art will readily appreciate that a device for orthopedic measurements, e.g. device 300, can be disposable as described above.

Referring now to FIGS. 12-15, the invention also provides a method of performing orthopedic measurements without spacers 136, as described above. As shown in FIG. 12, instead of spacers 136, tacks 336 are used. FIG. 12 shows a spinal model showing a first tack 336 and a second tack 336 placed in the spine. Those skilled in the art will readily appreciate that there are many scenarios that require orthopedic in-situ measurements without also requiring the insertion of spacers 136, as was discussed above. By using tacks 336 instead of spacers 136, device 300 can be used to take a variety of orthopedic measurements.

Figure 14:
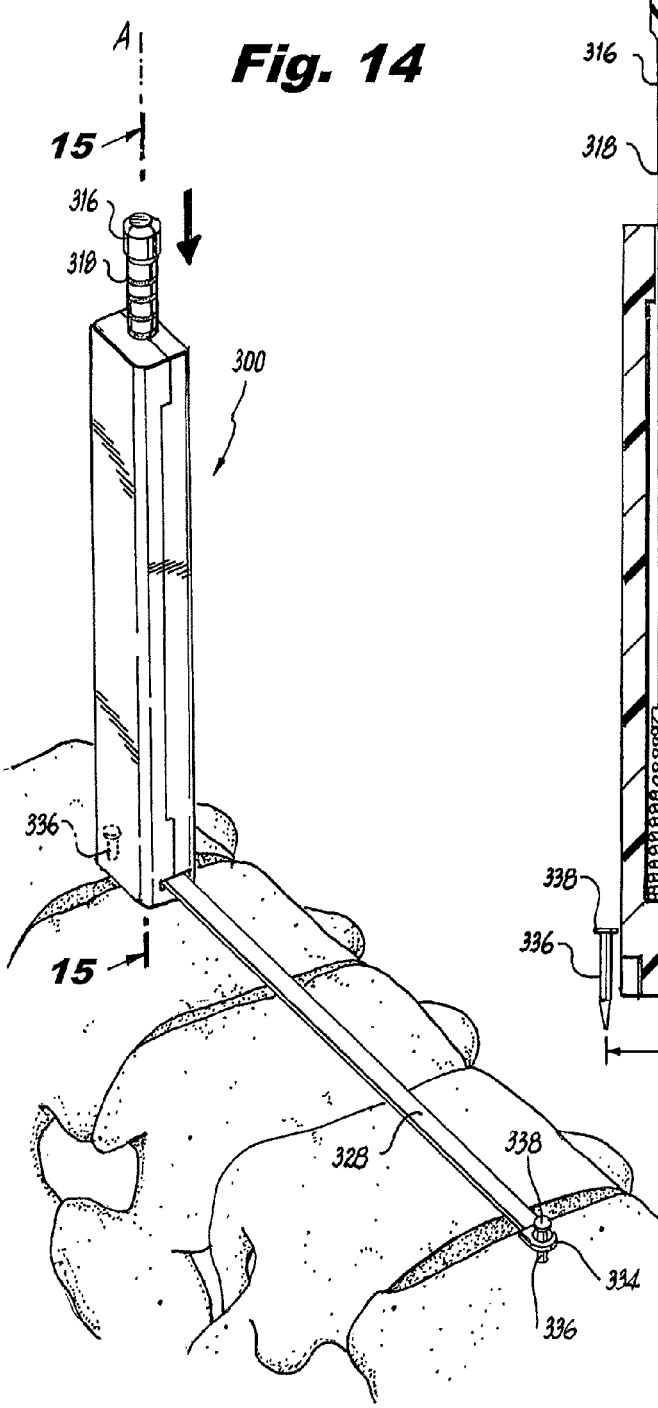
FIG. 14 is a perspective view of the spinal model of FIG. 12, showing a step of moving the device of FIG. 10 away from the first tack and deploying a flexible member.
Figure 15:
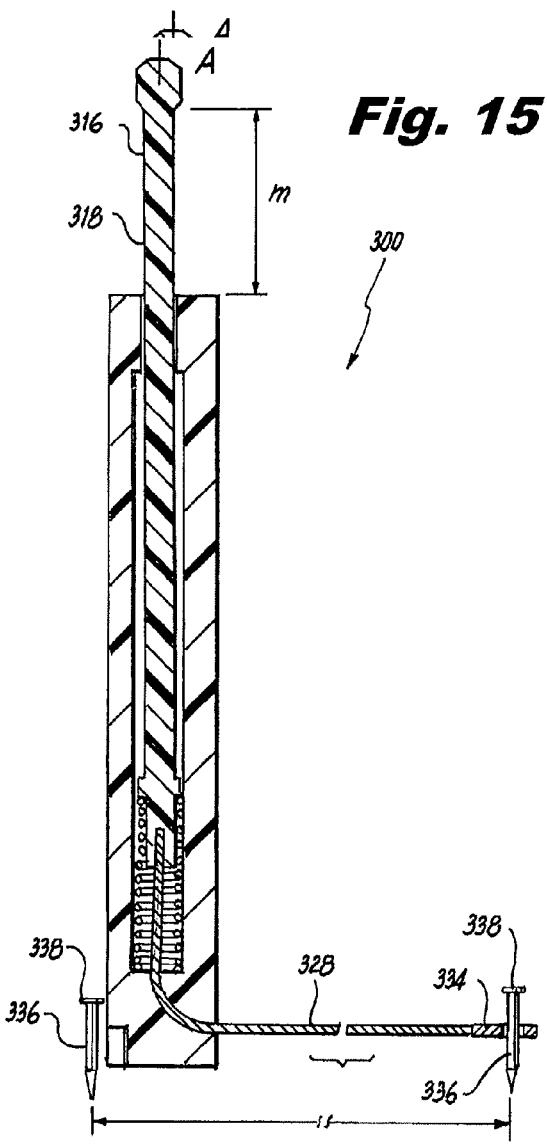
FIG. 15 is a cross-sectional view of the device of FIG. 10, showing the flexible member in a deployed position, and a measurement displayed on a measurement indicator.

With further reference to FIGS. 12-15, tacks 336 have heads 338 to accommodate for the securing of eyelet 334. The method includes inserting measurement tool, e.g. device 300, into an incision, securing an eyelet, e.g. eyelet 334, of the measurement tool on a first tack, e.g. tack 336, the eyelet being operatively connected to a flexible member, e.g. flexible member 328, as shown in FIG. 13, moving the measurement tool away from the first tack, wherein the movement deploys the flexible member and displays a measurement, e.g. measurement m, on the measurement indicator, e.g. measurement indicator 318, indicative of the distance between the measurement tool and the tack, as shown in FIGS. 14 and 15. When the back of device 300 contacts the second tack 336, as illustrated in FIG. 14, the span between the tacks can be determined from the displayed measurement m, e.g., by calibrating measurement m to account for the width of device 300 in the measurement direction. The sites where tacks 336 are placed can be selected as suitable sites ultimately used for bone screws, so measurement m can be used to directly select an implant with the proper spacing between screws, for example.

Those skilled in the art will readily appreciate that, although two tacks 336 are shown in FIGS. 12, and 14-15, the method can be performed with a single tack 336, or any other suitable number of tacks 336 appropriate for a given application. In addition, those skilled in the art will readily appreciate that tacks 336 without heads 338 and a variety of tack 336 shapes and sizes can be used. Further, those skilled in the art will readily appreciate that, kit 200, described above, for performing orthopedic measurements, can easily include alternative measurement tools, for example, device 300 and accompanying accessories such as tacks 336, as described above.

Those skilled in the art will readily appreciate that any other suitable orthopedic application can attain the advantages described herein without departing from the spirit and scope of the invention. For example, the orthopedic measurement tool can be used in the cervical spine, thoracic spine, lumbar spine, glenohumoral joint, hip joint, wrist, or in any other suitable location. The systems and methods of the invention increase measurement accuracy and provide for a less invasive way of performing orthopedic measurements.

Those skilled in the art will also readily appreciate that the methods and devices described above can also be applied or adapted to any other suitable procedure without departing from the spirit and scope of the invention. The devices, methods and systems of the present invention, as described above and shown in the drawings, provide for a device for performing orthopedic measurements with superior properties including accuracy, ease of use and ease of manufacture. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A device for orthopedic measurements, comprising:
   a main housing having a proximal end and a distal end, the proximal end having a top opening and the distal end having opposed first and second side openings, wherein the main housing defines a longitudinal axis and includes a main housing cavity;
   a center member disposed along the longitudinal axis within the main housing cavity, wherein the center member is configured and adapted to move along the longitudinal axis relative to the main housing;
   a measurement indicator operatively connected to the center member, configured and adapted to display a measurement of a distance;
   a cable including a first and a second end, each cable end having an eyelet, wherein the cable is threaded through the main housing cavity and wherein the eyelets are disposed proximate the first and second side openings, respectively, of the main housing, and are configured and adapted to be drawn away from the main housing extending the cable outward with respect to the side openings, and displaying a measurement on the measurement indicator;
   a center pulley wheel disposed on the center member within the main housing cavity between the measurement indicator and the distal end along the longitudinal axis, wherein the center pulley wheel is configured and adapted to move with the center member along the longitudinal axis relative to the main housing and to rotate about a pulley axis;
   a spring disposed in the main housing cavity along the longitudinal axis between the center pulley wheel and the distal end, wherein the spring is configured and adapted to bias the center member along the longitudinal axis away from the distal end of the main housing;
   a first side pulley wheel mounted within the main housing cavity proximate the first side opening configured and adapted to rotate about a pulley axis; and
   a second side pulley wheel mounted within the main housing cavity proximate the second side opening configured and adapted to rotate about a pulley axis, wherein the cable is threaded through the center, first side and second side pulley wheels, such that the first end extends through the first side opening and the second end extends through the second side opening.

2. A device for orthopedic measurements as recited in claim 1, wherein the cable is routed to move the center pulley wheel and the center member along the longitudinal axis relative to the main housing against a bias force of the spring when either or both of the eyelets extend outward from the main housing.

3. A device for orthopedic measurements as recited in claim 1, wherein the cable is threaded between the center pulley wheel and the center member, the first end threaded down through the main housing cavity, around the first side pulley wheel, and out through the first side opening, the second end threaded down through the main housing cavity, around the second side pulley wheel and out through the second side opening.

4. A device for orthopedic measurements as recited in claim 1, wherein the spring surrounds and operatively connects to the center member, wherein the spring is biased along the longitudinal axis such that the cable is biased toward an undeployed position.

5. A device for orthopedic measurements as recited in claim 1, wherein the cable is operatively connected to the center member so that movement of the center member against a bias force of the spring along the longitudinal axis drives the flexible member outward through at least one of the first and second side openings.

6. A device for orthopedic measurements as recited in claim 1, wherein a portion of the center member extends out of the main housing through the top opening at the proximal end.

7. A device for orthopedic measurements as recited in claim 6, wherein the measurement indicator is at least partially disposed on the portion of the center member that extends out of the main housing.

8. A device for orthopedic measurements as recited in claim 1, wherein each eyelet is disposed outside of the main housing cavity flush with the main housing and is larger than the side openings to prevent it from being drawn into the main housing cavity.

* * * * *